(12) United States Patent
Kwun et al.

(10) Patent No.: US 8,098,065 B2
(45) Date of Patent: Jan. 17, 2012

(54) MAGNETOSTRICTIVE SENSOR PROBE FOR GUIDED-WAVE INSPECTION AND MONITORING OF WIRE ROPES/CABLES AND ANCHOR RODS

(75) Inventors: Hegeon Kwun, San Antonio, TX (US); Albert J. Parvin, Jr., San Antonio, TX (US); Erika Christine Laiche, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 170 days.

(21) Appl. No.: 12/411,335

(22) Filed: Mar. 25, 2009

(65) Prior Publication Data

US 2010/0052670 A1 Mar. 4, 2010

Related U.S. Application Data

(63) Continuation-in-part of application No. 12/201,989, filed on Aug. 29, 2008.

(51) Int. Cl.
*G01N 27/82* (2006.01)
*G01H 11/04* (2006.01)

(52) U.S. Cl. .......................................... 324/240; 73/592

(58) Field of Classification Search .......... 324/200–263; 73/592
See application file for complete search history.

(56) References Cited

U.S. PATENT DOCUMENTS

| | | |
|---|---|---|
| 3,170,114 A | 2/1965 | Placke |
| 3,568,049 A | 3/1971 | Barton |
| 4,510,447 A | 4/1985 | Moyer |
| 4,543,528 A | 9/1985 | Baraona |
| 4,784,762 A | 11/1988 | Taliaferro |
| 4,866,424 A | 9/1989 | Parks |
| 4,916,394 A | 4/1990 | Thompson |
| 5,047,719 A | 9/1991 | Johnson et al. |
| 5,314,401 A | 5/1994 | Tepper |
| 5,334,937 A | 8/1994 | Peck et al. |
| 5,456,113 A | 10/1995 | Kwun et al. |
| 5,457,994 A | 10/1995 | Kwun et al. |

(Continued)

OTHER PUBLICATIONS

Light et al., Review Paper on Applications of Magnetostrictive Sensor Technology, 4th Middle East NDT Conference and Exhibition, Kingdom of Bahrain, Dec. 2007.*

(Continued)

*Primary Examiner* — Melissa Koval
*Assistant Examiner* — Daniel Miller
(74) *Attorney, Agent, or Firm* — Kammer Browning PLLC

(57) ABSTRACT

An economical, flexible, magnetostrictive sensor (MsS) probe assembly for use on longitudinal cylindrical structures, for guided-wave, volumetric inspection of the structures is described. The paired flexible plate MsS probes each include a flexible strip of magnetostrictive material that is positioned and/or adhered to the base of a generally flat, flexible, conductor coil assembly, preferably with an elastomeric adhesive. The conductor coil assembly has a core composed of a thin flexible layer of metal and a thin bendable permanent magnet circuit. The flexible core is surrounded by a flat flexible cable (FFC) that is folded and looped over the layers of the core. The exposed conductors at the ends of the FFC are shifted from each other by one conductor spacing and joined together so that the parallel conductors in the FFC form a flat, flexible, continuous coil. The probe assemblies may preferably be utilized in pairs and conformed to match the curved contours of the cylindrical surface of the structure under investigation in a manner that is specifically tailored for wire rope, cable, and anchor rod type applications.

8 Claims, 3 Drawing Sheets

U.S. PATENT DOCUMENTS

| | | | |
|---|---|---|---|
| 5,479,099 | A | 12/1995 | Jiles et al. |
| 5,581,037 | A | 12/1996 | Kwun et al. |
| 5,841,277 | A | 11/1998 | Hedengren et al. |
| 6,294,912 | B1 | 9/2001 | Kwun |
| 6,373,245 | B1 | 4/2002 | Kwun et al. |
| 6,373,252 | B1 | 4/2002 | Eslambolchi et al. |
| 6,396,262 | B2 | 5/2002 | Light et al. |
| 6,429,650 | B1 | 8/2002 | Kwun et al. |
| 6,624,628 | B1 | 9/2003 | Kwun et al. |
| 6,680,619 | B1 | 1/2004 | Horn |
| 6,799,466 | B2 | 10/2004 | Chinn |
| 6,812,707 | B2 | 11/2004 | Yonezawa et al. |
| 6,917,196 | B2 | 7/2005 | Kwun et al. |
| 6,967,478 | B2 | 11/2005 | Wayman et al. |
| 7,053,854 | B2 | 5/2006 | Plettner et al. |
| 7,183,764 | B2 | 2/2007 | Goldfine et al. |
| 7,375,514 | B2 | 5/2008 | Rempt et al. |
| 7,821,258 | B2 * | 10/2010 | Vinogradov ............... 324/240 |
| 7,852,073 | B2 * | 12/2010 | Kwun et al. ............... 324/262 |
| 2004/0016299 | A1 | 1/2004 | Glascock et al. |
| 2005/0208249 | A1 * | 9/2005 | Wen et al. ............... 428/40.1 |
| 2007/0100579 | A1 | 5/2007 | Rempt et al. |
| 2008/0071496 | A1 | 3/2008 | Glascock |
| 2009/0021253 | A1 * | 1/2009 | Kwun et al. ............... 324/238 |

OTHER PUBLICATIONS

"circumference, n.", Oxford English Dictionary, 2nd Edition 1989, online version Sep. 2011, Oxford University Press, accessed Oct. 13, 2011 at <http://www.oed.com/view/Entry/33281?rskey=Qu6s7E&result=1&isAdvanced=false>.*

* cited by examiner

MAGNETOSTRICTIVE SENSOR PROBE FOR GUIDED-WAVE INSPECTION AND MONITORING OF WIRE ROPES/CABLES AND ANCHOR RODS

CROSS REFERENCE TO RELATED APPLICATIONS

This application claims the benefit under 35 USC §120 of U.S. patent application Ser. No. 12/201,989; filed: Aug. 29, 2008 now U.S. Pat. No. 7,913,562.

BACKGROUND OF THE INVENTION

1. Field of the Invention

The present invention relates generally to methods and systems for non-destructive testing and inspection of wire ropes, wire cables, anchor rods and similar longitudinal cylindrical structures. The present invention relates more specifically to a magnetostrictive sensor probe for use on curved longitudinal cylindrical structural surfaces for guided wave inspection of the structure.

2. Description of the Related Art

Long-range, guided-wave inspection technology is an emerging technology that has the capability of quickly surveying a large volume of a structure for defects and providing comprehensive condition information on the integrity of the structure. Using relatively low-frequency (typically under 200 kHz) guided-waves in the pulse-echo testing mode, this technology performs a 100% volumetric examination of a large area of a structure and detects and locates internal and external defects in the area around a given test position. In above-ground pipelines, for example, a test range of more than 500 feet can be achieved in one direction for detecting 2% to 3% defects from a given test position. In this case, percent refers to the circumferential cross-sectional area of the defect relative to the total pipe wall cross section. In plate-type structures, a test range of more than 30 feet in one direction can be achieved. In wire ropes and cables, a 300 foot longitudinal measurement in one direction can be achieved.

This guided-wave inspection technology, including the magnetostrictive sensor (MsS) technology developed at Southwest Research Institute in San Antonio, Tex., is now widely used for testing piping networks in processing plants such as refineries and chemical plants, as well as for testing plate-type structures such as containment vessels walls and the like. The MsS technology is the only such guided-wave inspection technology that is applied to structures of many different geometries (e.g. pipe, tube, plate, rod, and cable) using a common approach with the same basic instrumentation.

For inspection of elongated structures (such as piping, tubing, rods, or cables), the Magnetostrictive Sensor (MsS) technology uses probes that are generally structured of a length of ribbon cable that encircles the structure's circumference along with a coil adapter that turns the parallel conductors in the ribbon cable into a continuous coil. For inspection of plate-type structures, plate MsS probes in the form of core type probes or flat coil type probes are used. Plate MsS probes in the form of core type probes are disclosed and described in U.S. Pat. No. 6,294,912 entitled Method and Apparatus for Non-Destructive Inspection of Plate Type Ferromagnetic Structures Using Magnetostrictive Techniques, the disclosure of which is incorporated herein in its entirety by reference. Plate magnetostrictive sensor probes in the form of flat coil type probes are disclosed and described in U.S. Pat. No. 6,396,262 entitled Method and Apparatus for Short Term Inspection or Long Term Structural Health Monitoring, the disclosure of which is incorporated herein in its entirety by reference.

Wire ropes and cables are widely used in various structures as important load carrying members. Examples of such longitudinal cylindrical structures include main cables and suspender ropes in suspension bridges, mooring lines in offshore platforms, guy lines for towers, dragline support ropes, and aerial tramway cables. In addition, wire ropes and cables are used in the electric power industry as transmission lines or ground wires.

The magnetostrictive sensor (MsS) technology developed by Southwest Research Institute (SwRI) was originally designed for guided-wave wire rope and cable inspections (U.S. Pat. Nos. 5,456,113 and 5,547,994). More recently, the MsS System is in use for commercial suspension bridge cable inspection services. The existing MsS method generates (and detects) longitudinal guided waves directly in the wires comprising the rope/cable using MsS coils that encircle the rope/cable and DC biasing magnetic circuits (made of either electromagnets or permanent magnets) placed directly on the rope/cable.

The DC biasing magnets necessary for such systems are generally heavy and require careful handling. In addition, the high cost of biasing magnets (a few thousand dollars each) is a drawback for permanent installation of the MsS for long-term structural health monitoring (SHM) of ropes/cables. A further complication exists if the ropes/cables are made of non-ferrous materials or have poor magnetostrictive properties for guided-wave generation and detection. In such cases the ropes/cables may need to be plated or bonded with a layer of magnetostrictive material such as nickel.

Anchor rods are long, slender, tension members that are typically driven into the ground and secured in position by an additional member (called a "cleat") attached to the rod end. The cleat may be a concrete block, a steel plate, or a steel frame. Typical sizes of anchor rods range from about 7 to 20 feet in length and ¾-2 inches in diameter. Anchor rods are typically made of galvanized structural steel, although a number are made of non-ferrous materials.

During the service life of guyed towers or poles, anchor rods may corrode along their length and thereby lose the capacity to hold the guyed structure, which could lead to catastrophic collapse of the structure. The MsS Technique may be used to inspect these anchor rods from the above-ground exposed section of the anchor rod without requiring costly excavation. Similar to the MsS wire rope/cable inspection, the present method generates longitudinal guided waves directly in the anchor rod using encircling coils and DC biasing magnetostrictive properties. Because of the higher signal amplitudes generated, this invention will also improve the results of anchor rod inspections.

3. Background on the Magnetostrictive Effect

The magnetostrictive effect is a property peculiar to ferromagnetic materials. The magnetostrictive effect refers to the phenomena of physical, dimensional change associated with variations in magnetization. The effect is widely used to make vibrating elements for such things as sonar transducers, hydrophones, and magnetostrictive delay lines for electric signals. The magnetostrictive effect actually describes physical/magnetic interactions that can occur in two directions. The Villari effect occurs when stress waves or mechanical waves within a ferromagnetic material cause abrupt, local dimensional changes in the material which, when they occur within an established magnetic field, can generate a magnetic flux change detectable by a receiving coil in the vicinity. The Joule effect, being the reverse of the Villari effect, occurs when a changing magnetic flux induces a mechanical vibrational motion in a ferromagnetic material through the generation of a mechanical wave or stress wave. Typically, the Joule effect is achieved by passing a current of varying magnitude through a coil placed within a static magnetic field thereby modifying the magnetic field and imparting mechanical waves into a magnetostrictive material present in that field. These mechanical or stress waves then propagate not only through the portion of the magnetostrictive material adjacent to the generating coil but also into and through any further materials in mechanical contact with the magnetostrictive material. In this way, non-ferromagnetic and/or non-magnetostrictive materials can serve as conduits for the mechanical waves or stress waves that can thereafter be measured by directing them through these magnetostrictive "wave guides" placed proximate to the magnetostrictive sensor element.

The advantages of magnetostrictive sensors over other types of vibrational sensors become quite clear when the structure of such sensors is described. All of the components typically utilized in magnetostrictive sensors are temperature, pressure, and environment-resistant in ways that many other types of sensors, such as piezoelectric based sensors, are not. High temperature, permanent magnets, magnetic coils, and ferromagnetic materials are quite easy to produce in a variety of configurations. Further, although evidence from the previous applications of magnetostrictive sensors would indicate the contrary, magnetostrictive sensors are capable of detecting mechanical waves and translating them into signals that are subject to very fine analysis and discrimination.

Examples of efforts that have been made in the past to provide systems and methods for positioning sensors in connection with the inspection of longitudinal cylindrical structures such as pipes and tubes include those disclosed in the following U.S. patents:

U.S. Pat. No. 4,543,528 issued to Baraona on Sep. 24, 1985 entitled Flexible Probe Assembly for Use in Non-Destructive Testing of a Convex Workpiece Surface describes a complicated frame structure that includes a flexible array of sensor heads that are arranged I tension to conform to the pipe when directed against its convex surface. Multiple sensor heads are required in order to provide compliance with the curved surface of the pipe.

U.S. Pat. No. 7,183,674 issued to Goldfine et al. on Feb. 27, 2007 entitled Method for Inspecting a Channel Using a Flexible Sensor describes a system and method for the inspection of components having limited access utilizing a pressurized elastic support structure to position a number of small sensor probes. The probes themselves are not specifically identified as flexible in nature as much as being small enough to be urged against the interior surfaces of a channel using the inflatable elastic structure.

U.S. Pat. No. 7,375,514 issued to Rempt et al. on May 20, 2008 entitled Flexible Handheld MR Scanning Array for Cracks/Flaws describes an NDE device with a sensor probe constructed on a flexible membrane. A frame supports the membrane and incorporates wheels for translation across the surface being inspected. The device is primarily directed to smoothly curved surfaces as may typically be found in aircraft structures.

U.S. Pat. No. 6,967,478 issued to Wayman et al. on Nov. 22, 2005 entitled Pipe Condition Detecting Apparatus describes a fully encircling array of individual sensors for placement in contact with the external wall of a pipeline. The device includes means for inducing and detecting magnetic flux at a location on the pipeline and determining whether changes in magnetic flux reflect changes in the condition of the pipe wall.

U.S. Pat. No. 5,334,937 issued to Peck et al. on Aug. 2, 1994 entitled Magnetic Field Gradient Coil and Assembly describes a magnetic field gradient coil for use in imaging techniques over and within a cylindrical structure. The coil is established through the use of an array of parallel conductors oriented in varying directions around and along the length of the cylindrical structure.

U.S. Pat. No. 6,680,619 issued to Horn on Jan. 20, 2004 entitled Sensoring Device for Monitoring Potential on Corrosion Threatened Objects describes an array of individual sensors positioned on an encircling band about a cylindrical structure such as a pipe. A number of individual cables are connected to the plurality of sensors arranged in a matrix defining measurement points with specifically identified distances.

U.S. Pat. No. 4,784,762 issued to Taliaferro entitled Magnetic Trap describes a method for positioning a Hall Effect sensor on the external surface of a cylindrical pipe. The structure includes a magnetic trap positioned in conjunction with a magnetically transparent sheet on one side of which a magnet is mounted to produce a magnetic field. The Hall Effect sensor is positioned adjacent the magnet to sense the magnetic field.

U.S. Pat. No. 3,568,049 issued to Barton on Mar. 2, 1971 entitled Adjustable Search Shoe for Use in Non-Destructing Testing of Tubular Members describes a sensor structure that includes an object engaging surface that may be mechanically adjusted to change its curvature so as to conform to the wall of the pipe or tubular object under inspection.

U.S. Pat. No. 5,479,099 issued to Jiles et al. on Dec. 26, 1995 entitled Magnetic Inspection Heads Suited for Contoured or Irregular Surfaces describes an arrangement of coils associated with an array of moveable pins within an assembly that is positioned against the curved surface of a pipe or tube. The pins adjust their position according to contact with the external circumference of the pipe and thereby establish a conformed contact surface for the sensor on the magnetic inspection head.

In general, the prior efforts in the field associated with cylindrical structures have been directed to partial circumference sensor structures only where the type of interrogating signal is easily suited to such configurations. That is, none of the previous efforts at partial circumferential orientation have provided suitable sensor adherence structures for use in conjunction with long-range guided-waves. These interrogating waves have heretofore been limited to propagation from sensor structures that circumferentially surround the pipe or tube. In a similar manner, the prior efforts in the field utilizing plate type MsS probes have been limited to individual use on planar structures or within arrays utilizing complex probes and support frame mechanisms, as well as complex multi-sensor operation. None of the previous efforts at either partial circumference sensor structures, or arrays of plate MsS probes, have accomplished the efficient use of such probes at a lower cost and with greater versatility.

It would, therefore, be desirable to have not only a flexible plate type MsS probe that could be used alone or in conjunction with a number of additional probes for investigation of structures having a variety of surface curvatures, but additionally it would be desirable if such a probe was small in size, both for operational optimization and manufacturing efficiency. Once again, while such probe structures could be constructed according to some of the approaches that have been carried out before (in the referenced patent disclosures), such can generally be accomplished only through a significant increase in complexity, both for the probe and the instrumentation associated with its use. The preference would be to simplify the probe's construction and its functionality such that it would be not only simple to utilize in its application (i.e., its placement and positioning on the structure to be investigated) but also in its instrumentation and the ability of standard systems to generate guided-wave interrogation signals sufficient to identify anomalies within the structures at significant distances.

It would also be desirable to have a sensor structure that was economical to manufacture and versatile in its use. The simplicity and ruggedness of its construction would contribute to the requirement for variability in the number of such sensors that might be used in a single structural investigation, while a compact size and flexibility would contribute to the versatility of use in conjunction with a wide range of curved or planar surfaces. To overcome the shortcomings of existing MsS Systems and methods, and to further expand the use of the MsS for long-term SHM of ropes/cables, it would be desirous to have an MsS probe that is lightweight, relatively inexpensive, and is operable independent of the rope/cable material.

In the present invention, systems and methods for constructing and using a plate MsS probe for guided-wave inspection of a variety of longitudinal cylindrical structures are described. The basic probe component configuration is based upon that structure described in the parent Application, U.S. patent application Ser. No. 12/201,989; filed: Aug. 29, 2008; entitled Flexible Plate Magnetostrictive Sensor Probe for Guided-Wave Inspection of Structures; the disclosure of which is incorporated herein in its entirety by reference. The systems and methods are further built upon existing magnetostrictive sensor (MsS) methods and devices, particularly the thin magnetostrictive strip approach (described in U.S. Pat. No. 6,396,262, entitled Method and Apparatus for Short Term Inspection or Long Term Structural Health Monitoring; U.S. Pat. No. 6,429,650, entitled Method and Apparatus Generating and Detecting Torsional Wave Inspection of Pipes and Tubes; and U.S. Pat. No. 6,917,196, also entitled Method and Apparatus Generating and Detecting Torsional Wave Inspection of Pipes and Tubes, the disclosures of which are each incorporated herein in their entirety by reference), and the plate MsS probe (described in U.S. Pat. No. 6,294,912, entitled Method and Apparatus for Nondestructive Inspection of Plate Type Ferromagnetic Structures using Magnetostrictive Techniques, the disclosure of which is incorporated herein in its entirety by reference), but modified and made less expensive and more versatile to fit the specific purposes of the present invention.

SUMMARY OF THE INVENTION

The present invention therefore describes an economical, flexible, magnetostrictive sensor (MsS) probe assembly for use on longitudinal cylindrical structures, for guided-wave, volumetric inspection of the structures. The flexible plate MsS probes include a flexible strip of magnetostrictive material that is positioned and/or adhered to the base of a generally flat, flexible, conductor coil assembly, preferably with an elastomeric adhesive. The conductor coil assembly has a core that is composed of a thin flexible layer of metal, and a thin and bendable permanent magnet circuit. The flexible core is surrounded (top, bottom, and on the longitudinal ends) by a flat flexible cable (FFC) that is folded and looped over the layers of the core. The exposed conductors at the ends of the FFC are shifted from each other by one conductor spacing and joined together so that the parallel conductors in the FFC form a flat, flexible, continuous coil. The probe assemblies may be utilized in pairs and conformed to match the curved contours of the cylindrical surface of the structure under investigation. This invention describes an MsS probe that has the desired characteristics; namely light-weight, relatively inexpensive, and operable independently of the rope/cable material. As indicated above, this invention is an extension of the flexible plate probe described in the co-pending U.S. patent application Ser. No. 12/201,989, as one embodiment that is tailored for wire rope and cable applications.

Although the primary purpose of this invention is for wire rope/cable inspection and monitoring, it is also applicable for MsS guided-wave inspection of anchor rods. Many tall towers or poles are supported by guy wires anchored to the earth with rods. Examples are towers for antennas and high voltage electric transmission lines and electric distribution poles. Further features of both the system of the present invention and its method of use will become apparent from the following detailed description with reference to the appended drawing figures.

BRIEF DESCRIPTION OF THE DRAWINGS

The accompanying figures will give a fuller description and a better understanding of the details and advantages of the present invention. The drawing figures appended may be briefly described as follows.

DETAILED DESCRIPTION OF THE PREFERRED EMBODIMENTS

Figure 1:
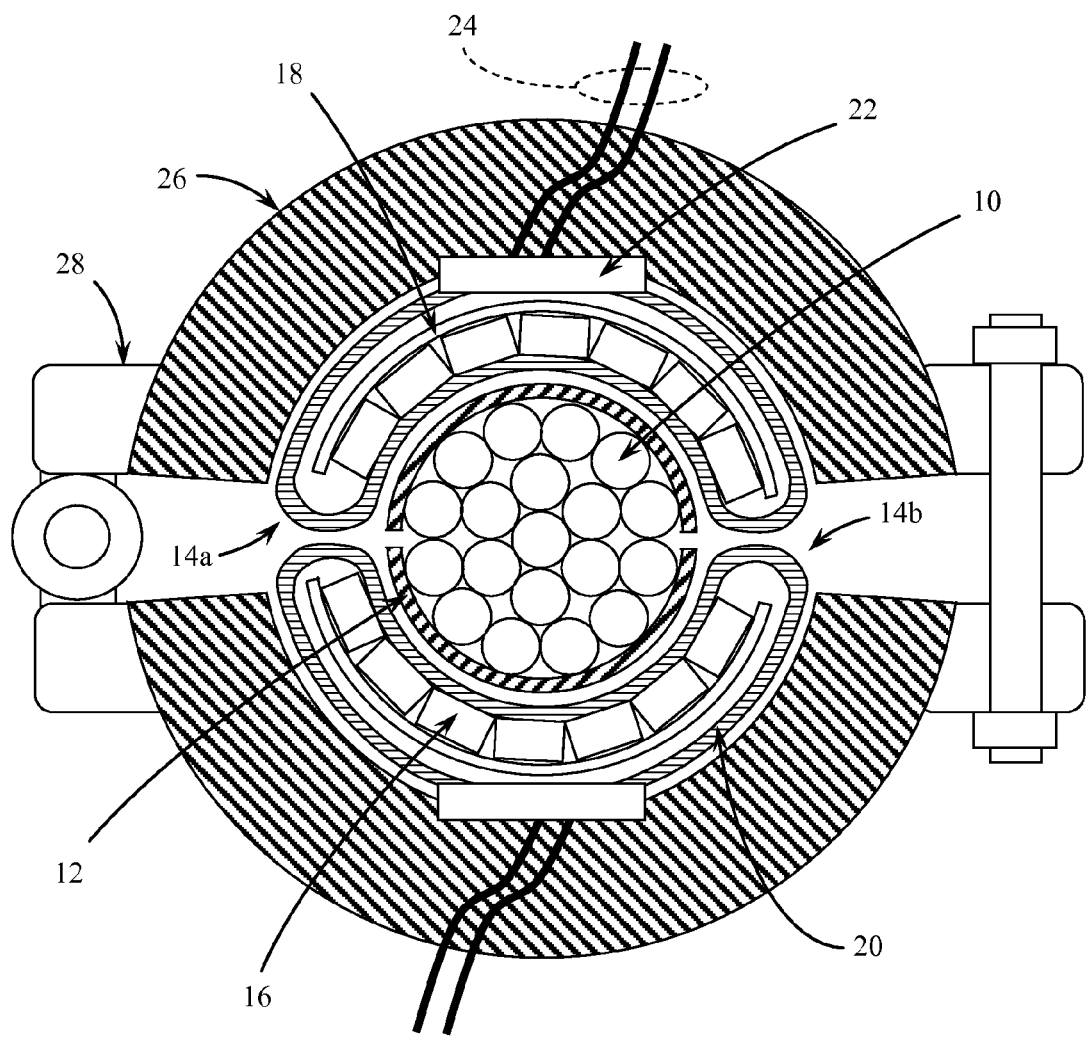
FIG. 1 is a partial cross-sectional view of the magnetostrictive sensor probe assembly of the present invention shown using a pair of sensor probes positioned on either side of a larger cylindrical bundle of wire rope.
Figure 2:
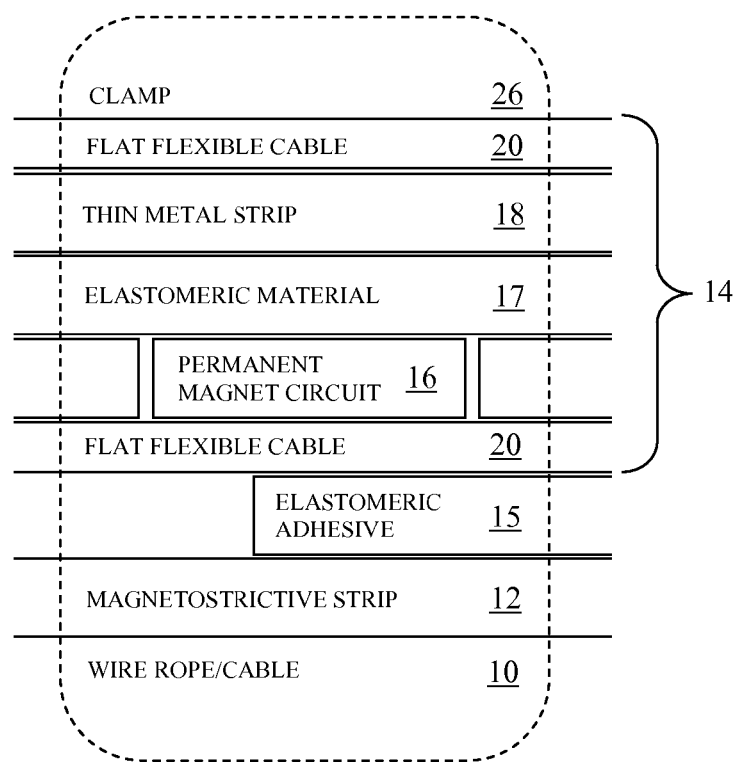
FIG. 2 is a schematic block diagram disclosing the functional layers of the magnetostrictive sensor probe assembly of the present invention as shown.
Figure 3:
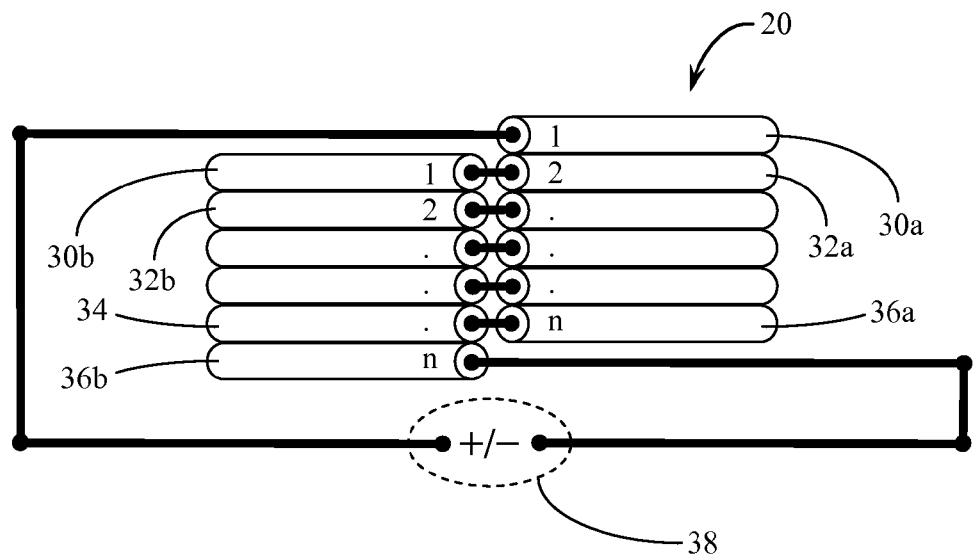
FIG. 3 is a schematic representation of the structure of the flat flexible cable (FFC) coil conductor connection of the present invention.

Reference is made first to FIG. 1 for a brief description of the basic structure and function of the magnetostrictive sensor probe assembly of the present invention. FIG. 1 illustrates in a partial cross-sectional view, a pair of flexible plate MsS probes of the present invention positioned on either side of a longitudinal cylindrical structure (a larger, wound wire cable in this case). Each of the probe's layered structures may best be described according to its cross-sectional configuration which, as shown functionally in FIG. 2. This structure is functionally composed of thin layers of: a magnetostrictive strip; a flat flexible cable (FFC); a permanent magnetic circuit comprising an array of small permanent magnets pieces (preferably set in an elastomeric material); and a metal strip. The FFC is folded and looped over the balance of the layers. The exposed conductors at the ends of the FFC are shifted from each other by one conductor spacing and joined together so that the parallel conductors in the FFC form a continuous coil as illustrated in FIG. 3, and described in more detail below.

A schematic illustration of the MsS probe assembly of the present invention for the inspection and long-term monitoring of a wire rope/cable 10 is shown in FIG. 1. The probe assembly is divided into two halves 14a and 14b that are identical and symmetrical. Each half includes: the above mentioned thin layers of a magnetostrictive strip 12 with a high transduction efficiency, a flat flexible cable (FFC) 20 containing multiple parallel conductors at a small spacing (for example 0.5 mm), an array of small permanent magnets 16, an elastomeric material (such as silicon rubber) (not shown), and a thin layer of metal shield 18. The magnetostrictive strip 12 is attached to the FFC 20 using an elastomeric adhesive (such as silicon or polyurethane) (not show for clarity in FIG. 1). The FFC 20 is folded and looped over the balance of the layers. The ends of the FFC 20 are electrically joined to a printed circuit board with FFC connectors 22. The circuit board is designed to form a continuous coil as illustrated in FIG. 2. Electric wires 24 are then soldered to the ends of this coil 20 thus formed to connect the probe to the requisite MsS Instrumentation.

Also disclosed in FIG. 1 is the manner of securing the "clam-shell" like halves of the probe assembly of the present invention to the wire rope/cable 10 under inspection or monitoring. A variety of mechanisms may be utilized to position and retain the probe assembly on the cylindrical structure. In the example show in FIG. 1, a pair of clamp elements 26, removably connected together using clamp connector elements 28, provide a simple yet rugged means for securing the assembly to the wire rope/cable. Other means for securing the probe assembly are contemplated, such as belts, straps, cable ties, and the like.

FIG. 2 discloses in greater detail the manner in which the various layers of the probe assembly function to achieve the generation of guided-waves into the structure being investigated and to receive reflected guided-waves back from the structure to be detected within the NDE instrumentation. FIG. 2 provides a representative cross-section of one of the two layered structures of the flexible probe assembly of the present invention. In this view, magnetostrictive strip 12 is shown as it would be placed in position against the surface of the structure (wire rope/cable 10) being investigated. The conductor coil assembly 14, comprising the multiple layers described in more detail below, is positioned over magnetostrictive strip 12 and adhered thereto by way of elastomeric adhesive 15. Some intermittent spacing with regard to the placement of elastomeric adhesive 15 may facilitate the lateral movement of conductor coil assembly 14 with respect to magnetostrictive strip 12, as may be necessitated through the bending of the probe.

Conductor coil assembly 14 is itself comprised of internal layers surrounded by flat flexible cable 20 as described above. In this cross-sectional view it is the lower side layer of flat flexible cable 20 that provides the contact surface with magnetostrictive strip 12 through elastomeric adhesive 15. Within flat flexible cable 20 are the layers comprising thin flexible metal strip 18, elastomeric material 17, and permanent magnet circuit 16. Once again, each of these layers is constructed to allow some lateral movement of the layers upon bending of the flexible sensor probe so as to prevent buckling or separation of the layers during use. Each constituent layers in the probe is flexible and can move from each other. The probe therefore can accommodate a large range of surface curvatures.

FIG. 3 discloses in greater detail the manner in which the flat flexible cable (FFC) is arranged to create a continuous loop coil. Flat flexible cable, sometimes referred to as "ribbon cable," is commonly used with electronic circuits, often to connect one circuit board to another where a flexible path is required. Such cable is therefore relatively inexpensive although its use is almost universally limited to parallel path conductor connection. In the present invention, the FFC is used to easily establish a continuous conductor coil (that remains flexible and flat) by connecting the ends of the flat cable together after shifting the conductors by one conductor path. In this manner, as shown in FIG. 3, the first conductor 30a of one end of the cable 20 is left free for external connection while the second conductor 32a of the first end is connected to the first conductor 30b of the second end of the cable. In this manner, the $n^{th}$ conductor 36a of the first end of the cable 20 is connected to the n−1 conductor 34 of the second end of the cable 20, leaving the $n^{th}$ conductor 36b of the second end free for external connection.

When the free conductors (one from each end of the flat cable) are connected to a current source 38, the device functions as a continuous conductor coil suitable for establishing a current varying dependent magnetic field within the volume inside and around the coil. It is this magnetic field fluctuation that initiates the magnetostrictive effect in the magnetostrictive strip of the sensor probe assembly of the present invention. The reverse magnetostrictive effect allows the sensor probe to detect the guided waves within the object structure under investigation as they move through the magnetostrictive strip and measurably alter the magnetic field within and about the coil.

The permanent magnet array in the probe provides a DC bias magnetic field required for MsS longitudinal guided-wave generation and detection. The elastomeric material layer helps to evenly distribute the pressing force over the entire contacting surface of the magnetostrictive strip and, thus, achieve uniform mechanical coupling across the contacting surface. The metal shield screens off the time varying magnetic field produced by the upper part of the coil. To facilitate the coupling between the magnetostrictive strip and the ground wire, an intermediary compliant coupling layer (not shown in FIG. 1) may be placed on the magnetostrictive layer.

In use, the probe assembly would be placed around a wire rope/cable under testing and compressed against the rope/cable with the clamping device as described. The guided waves generated in the magnetostrictive strip in the probe would then couple to the rope/cable and propagate along its length. Any reflected signals that return to the MsS probe would then be detected in reverse order.

Figure 4:
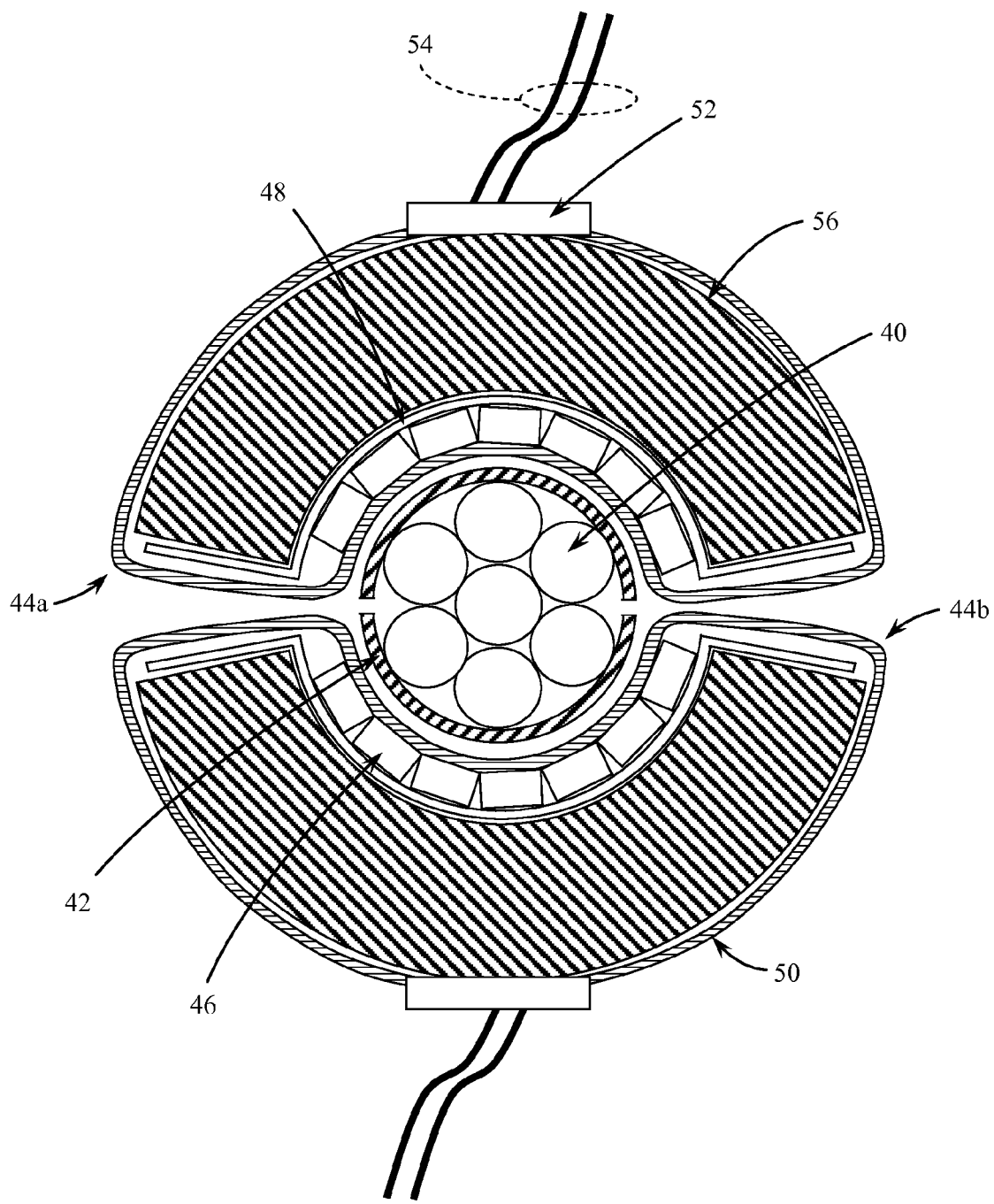
FIG. 4 is a partial cross-sectional view of an alternate embodiment of the magnetostrictive sensor probe assembly of the present invention shown using a pair of sensor probes positioned on either side of a smaller cylindrical bundle of wire rope.

A variation of the probe design illustrated in FIG. 1 is shown in FIG. 4 for small diameter wire rope applications, for example, less then 25 mm. A schematic illustration of an alternate MsS probe assembly of the present invention, for the inspection and long-term monitoring of a smaller wire rope/cable 40 is shown in FIG. 4. The probe assembly is again divided into two halves 44a and 44b that are identical and symmetrical. Each half includes: the above mentioned thin layers of a magnetostrictive strip 42 with a high transduction efficiency, a flat flexible cable (FFC) 50 containing multiple parallel conductors at a small spacing, an array of small permanent magnets 46, an elastomeric material (such as silicon rubber) (not shown), and a thin layer of metal shield 48. The magnetostrictive strip 42 is attached to the FFC 50 using an elastomeric adhesive (such as silicon or polyurethane) (again not show for clarity in FIG. 4). The FFC 50 is folded and looped over the balance of the layers. The ends of the FFC 50 are electrically joined to a printed circuit board with FFC connectors 52. Electric wires 54 are then soldered to the ends of this coil 50 thus formed to connect the probe assembly to the requisite MsS Instrumentation.

In this alternate embodiment, the probe assemblies are arranged around a semi-circular, annular frame 56. The clamp elements shown in FIG. 1 may then be placed over the probe assembly in FIG. 4. For long-term monitoring applications, the invention would be mechanically fastened and fixed in position on the rope/cable. In addition, to maintain the mechanical coupling of guided waves between the probe and the wire/cable, the probe could be adhesively bonded to the wire/cable.

Although the present invention has been described in terms of the foregoing preferred embodiments, this description has been provided by way of explanation only and is not intended to be construed as a limitation of the invention. Those skilled in the art will recognize modifications of the present invention and its methods of use that might accommodate specific rods, cables, wire ropes and other longitudinal cylindrical structures, and even specific magnetostrictive sensor configurations. Such modifications as to the structures under inspection or their specific curvatures or to the sensor structures, where such modifications are merely incidental to the specific NDE environment, do not necessarily depart from the spirit and scope of the underlying invention.

We claim:

1. A flexible plate-type magnetostrictive sensor (MsS) probe assembly for inspection of longitudinal cylindrical structures, the MsS probe assembly comprising:
   a pair of flat flexible cable (FFC) coil assemblies, the FFC coil assemblies each having a top face and a bottom face and comprising a length of flat flexible cable (FFC) having a plurality of parallel conductors, the FFC folded back on itself and connected one end to the other after shifting the plurality of parallel conductors by one, thereby creating a continuous conductor loop coil having first and second electrical connections, the coil assemblies positioned in a diametrically opposing configuration around a circumference of the longitudinal cylindrical structure to provide a single full encirclement of the longitudinal structure;
   a pair of flexible strips of magnetostrictive material, one of the flexible magnetostrictive strips adhered to the bottom face of each of the FFC coil assemblies between the coil assemblies and the longitudinal cylindrical structure; and
   a pair of clamp elements positioned in an opposing configuration around the pair of FFC coil assemblies;
   wherein time varying current in the FFC coil assemblies causes guided-waves to be generated in the magnetostrictive strips, which guided-waves, when the magnetostrictive strips are positioned against the surfaces of the longitudinal cylindrical structure, travel to and are reflected by anomalies in the structure under inspection.

2. The MsS probe assembly of claim 1 wherein the FFC coil assemblies each comprise:
   a flexible strip of metal having a top face and a bottom face; and
   a layer of elastomeric material positioned on the bottom face of the metal flexible strip;
   wherein the metal strip is positioned within the coil constructed by folding the
   FFC back on itself.

3. The MsS probe assembly of claim 2 wherein the FFC coil assemblies each further comprise:
   a thin permanent magnet array positioned on the layer of elastomeric material opposite from the flexible strip of metal, the permanent magnet array comprising an array of commonly oriented permanent magnets to establish a bias magnetic field in the magnetostrictive strip.

4. The MsS probe assembly of claim 1 wherein the pair of flexible strips of magnetostrictive material are adhered, one to each of the bottom faces of the FFC coil assemblies with an elastomeric adhesive.

5. The MsS probe assembly of claim 2 wherein the FFC coil assemblies each further comprise:
   an FFC connector block for receiving and electrically connecting the shifted plurality of parallel conductors of one end of the FFC to the other, the connector block further incorporating the first and second electrical connections to the FFC coil assembly.

6. The MsS probe assembly of claim 1 wherein the pair of clamp elements each comprise an element of semi-circular cross-section, removably connectable to each other around the pair of FFC coil assemblies and the pair of magnetostrictive strips, for urging the coil assemblies and magnetostrictive strips against the surface of the longitudinal cylindrical structure under investigation.

7. A flexible plate-type magnetostrictive sensor (MsS) probe assembly for inspection of longitudinal cylindrical structures, the MsS probe assembly comprising:
   (a) a pair of flat flexible cable (FFC) coil assemblies, the FFC coil assemblies each having a top face and a bottom face, the coil assemblies positioned in a diametrically opposing configuration around a circumference of the longitudinal structure to provide a single full encirclement of the longitudinal structure, the coil assemblies each comprising:
      (i) a length of flat flexible cable (FFC) having a plurality of parallel conductors, the FFC folded back on itself and connected one end to the other after shifting the plurality of parallel conductors by one, thereby creating a continuous conductor loop coil having first and second electrical connections;
      (ii) a flexible strip of metal having a top face and a bottom face; and
      (iii) a layer of elastomeric material positioned on the bottom face of the flexible metal strip;
   wherein the metal strip is positioned within the coil constructed by folding the FFC back on itself;
   (b) a pair of flexible strips of magnetostrictive material, one of the flexible magnetostrictive strips adhered to the bottom face of each of the FFC coil assemblies between the coil assemblies and the longitudinal cylindrical structure; and
   (c) a pair of clamp elements positioned in an opposing configuration around the pair of FFC coil assemblies, the pair of clamp elements each comprising an element of semi-circular cross-section, removably connectable to each other around the pair of FFC coil assemblies and the pair of magnetostrictive strips, for urging the coil assemblies and magnetostrictive strips against the surface of the longitudinal cylindrical structure under investigation;
   wherein time varying current in the FFC coil assemblies causes guided-waves to be generated in the magnetostrictive strips, which guided-waves, when the magnetostrictive strips are positioned against the surfaces of the structure, travel to and are reflected by anomalies in the structure under inspection.

8. The MsS probe assembly of claim 7 wherein the FFC coil assemblies each further comprise:
   a thin permanent magnet array positioned on the layer of elastomeric material opposite from the flexible strip of metal, the permanent magnet array comprising an array of commonly oriented permanent magnets to establish a bias magnetic field in the magnetostrictive strip.

* * * * *